United States Patent [19]

Collins et al.

[11] Patent Number: 4,534,339
[45] Date of Patent: Aug. 13, 1985

[54] ENDOSCOPE

[75] Inventors: Ian P. Collins, Welwyn; Douglas P. Fernie, Thriplow, both of England

[73] Assignee: Warner-Lambert Technologies, Inc., Dallas, Tex.

[21] Appl. No.: 542,611

[22] Filed: Oct. 17, 1983

[51] Int. Cl.³ .............................................. A61B 1/00
[52] U.S. Cl. ......................................................... 128/6
[58] Field of Search ...................................... 128/4–11

[56] References Cited

U.S. PATENT DOCUMENTS

| | | | |
|---|---|---|---|
| 3,100,482 | 8/1963 | Hett | 128/6 |
| 3,417,746 | 12/1968 | Moore et al. | 128/6 |
| 3,726,272 | 4/1973 | Fukami et al. | 128/6 |
| 4,203,430 | 5/1980 | Takahashi | 128/4 |
| 4,207,873 | 6/1980 | Kruy | 128/6 |
| 4,414,608 | 11/1983 | Furihata | 128/4 X |
| 4,416,268 | 11/1983 | Hagino | 128/6 |
| 4,461,282 | 7/1984 | Ouchi et al. | 128/4 |

Primary Examiner—William H. Grieb
Attorney, Agent, or Firm—Alan H. Spencer; Richard S. Strickler

[57] ABSTRACT

An endoscope has a shaft (4) detachably connected to a handle (2) to enable the shaft (4) to be detached for repair or maintenance. The shaft (4) and handle (2) are detachably connected by spring-loaded latches (10) in the handle which are frictionally engageable with pins (8) projecting from the coupling face of the shaft (4). An external locking sleeve (20) prevents inadvertent separation of the shaft and handle. Illuminating light and the image to be viewed are coupled across the handle/shaft interface by abutting ends of fiber optic bundles (76, 80, 86, 92). The shaft (4) can be flexed by adjustment of manual controls on the handle as a result of racks (40, 44) in the handle (2) exerting a pushing motion on racks (50, 52) in the shaft (4), this pushing motion being transmitted into a pulling action applied to flexure wires (66, 62) extending in the shaft by virtue of pinions (54, 56) interconnecting the two racks of each pair of racks (50, 52) in the shaft (4). An alternative embodiment (FIGS. 14 and 15) has meshing gears on the shaft and handle to transmit across the handle/shaft interface the motion which flexes the shaft.

29 Claims, 20 Drawing Figures

ENDOSCOPE

BACKGROUND OF THE INVENTION

This invention relates to endoscopes which are medical instruments for inspecting the cavities of internal organs.

A typical form of known endoscope has a handle from which extends a flexible shaft, terminating in a distal or operative end, which is inserted into a cavity to be inspected. Light is transmitted from the handle, through the shaft, to the distal end where the light emitted illuminates the cavity to be inspected. The image to be viewed is transmitted back up the shaft to the handle which is equipped with an eyepiece for this purpose. To enable the shaft to reach inaccessible locations, and to be capable of controlled adjusting movement, the shaft is flexible and incorporates wires which are pulled in a controlled way as a result of manual adjustment of remote knobs or wheels on the handle. Typically, there are two pairs of such wires passing within the shaft, one pair for flexing the shaft in one plane and the other pair for flexing the shaft in an orthogonal plane. Two independently rotatable knobs, or wheels, on the handle are respectively linked to the two pairs of wheels providing for adjustment of the distal end of the shaft in any direction. It is also usual to provide two tubes extending between the handle and the distal end of the shaft, one for leading air and water to the distal end of the shaft, and one for biopsy and suction.

When such a known endoscope needs repairing, the whole instrument is put out of action. To cover such a contingency, a doctor needs to keep a spare endoscope ready for use. The majority of faults develop in the endoscope shaft, but most of the cost of manufacture lies in the handle. The invention stems from the realization that it would be beneficial to make the shaft and handle detachable so that a faulty shaft can be replaced by a spare shaft, without the need to provide a duplicate handle.

SUMMARY OF THE INVENTION

According to the invention, an endoscope has a handle, a shaft with a flexible length terminating in a distal end, a proximal end of the shaft having a coupling face for detachable connection to a coupling face of the handle and the other end of the shaft being arranged to receive an optical image of a subject to be viewed, flexure control means operable on the handle for effecting controlled flexing of the shaft, first coupling means for mechanically coupling the shaft and handle, the first coupling means being capable of being released to allow the shaft and handle to be separated, second coupling means for transmitting illuminating light from the handle to the shaft, third coupling means for transmitting an optical image from the shaft to the handle, and fourth coupling means for transmitting from the handle to the shaft movement providing for the controlled flexing of the shaft.

Preferably, the first coupling means allows the shaft and handle to be pushed together but automatically prevent relative withdrawing movement of the shaft and handle. This may be achieved by a spring-loaded latch which frictionally engages a pin to prevent separating movement of the shaft and handle, the latch being manually movable to a release position to allow separation of the shaft and handle.

The third coupling means for transmitting the image may comprise a fiber optic bundle in the handle and a flexible fiber optic bundle in the shaft, at the coupling faces, the fiber optic bundles presenting ends which make face to face contact, or are brought into close face to face relationship, when the shaft and handle are connected together. The fiber optic bundle in the handle may be a fused fiber optic bundle which extends (conveniently in a straight line) from the coupling face of the handle to an eyepiece of the endoscope, the handle being formed with a groove to receive the fused fiber optic bundle. Alternatively, the third coupling means may comprise a fiber optic bundle which extends, without interruption from the shaft, through the handle and thence to the eyepiece, the length of fiber optic bundle within the handle being withdrawn therefrom when the shaft is separated from the handle. In a yet further alternative, the third coupling means comprises a flexible fiber optic bundle in the shaft and a lens within the handle, the lens transmitting the image from the coupling face of the shaft towards an eyepiece of the endoscope.

In the preferred embodiment to be described, the fourth coupling means relies on a pushing movement being transmitted from the handle to the shaft, reversing means being provided in the shaft to convert the pushing movement into a pulling movement applied to tension elements which extend within the shaft and which are operative when pulled to flex the shaft. The reversing means conveniently includes a pair of racks interconnected by a pinion, a pushing action on one of said racks being converted into a pulling action of the other of said racks by means of the pinion. An alternative envisaged is for the fourth coupling means to comprise toothed wheels mounted respectively on the coupling faces of the handle and of the shaft, the toothed wheels making meshing engagement when the shaft and handle are coupled together.

The satisfactory coupling of the various functions between the handle and shaft poses several design problems, both mechanical and optical. The preferred solutions are disclosed in the following specific description given with reference to the drawings.

An endoscope according to the invention will now be described, by way of example, with reference to the accompanying drawings in which.

Figure 5:
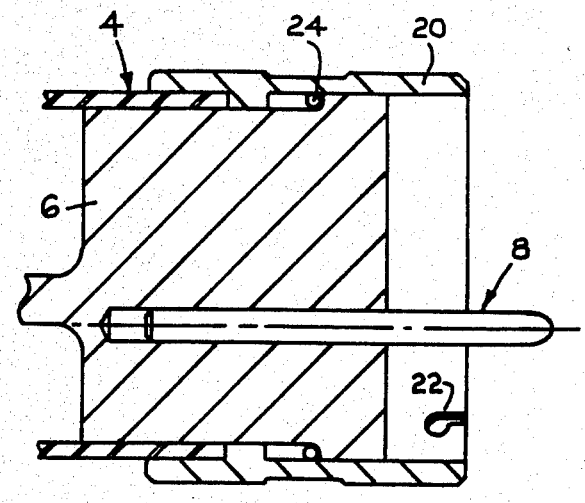
FIGS. 5 and 6 are fragmentary sectional side views showing the mechanical coupling means for coupling the shaft and handle.
Figure 6:
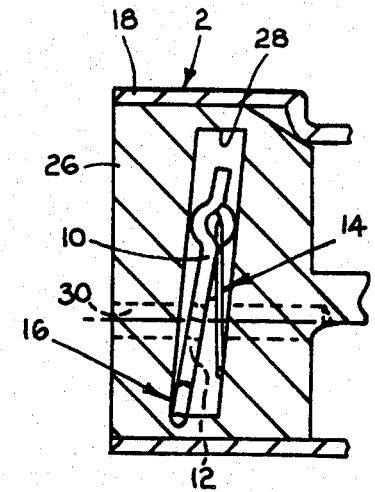
Figure 7:
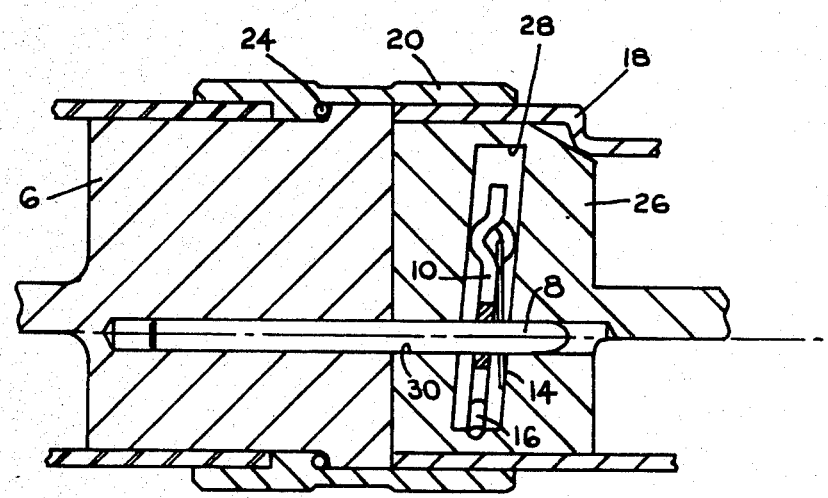
Figure 8:
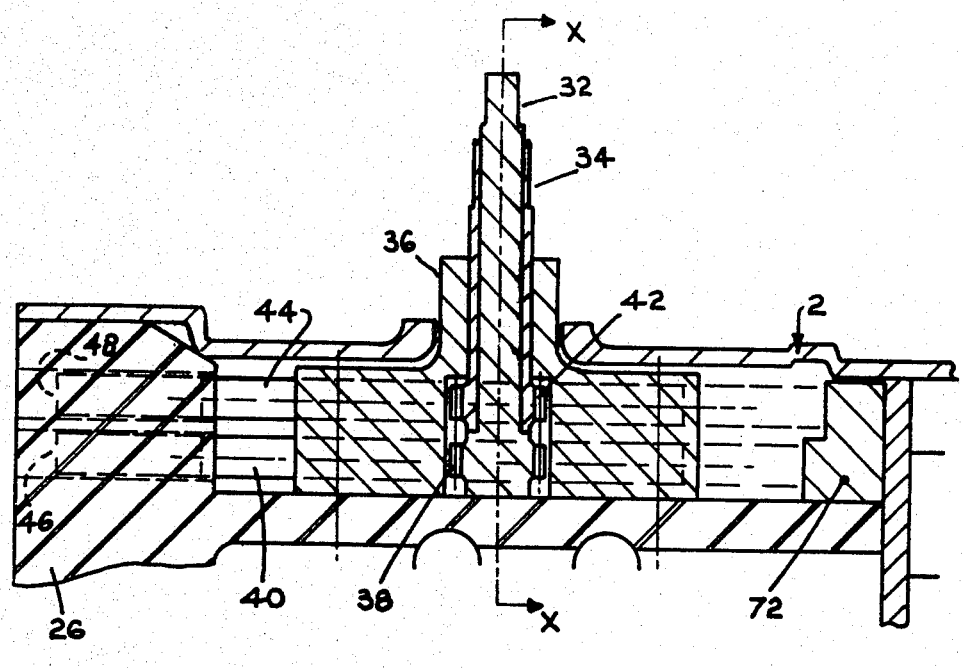
Figure 9:
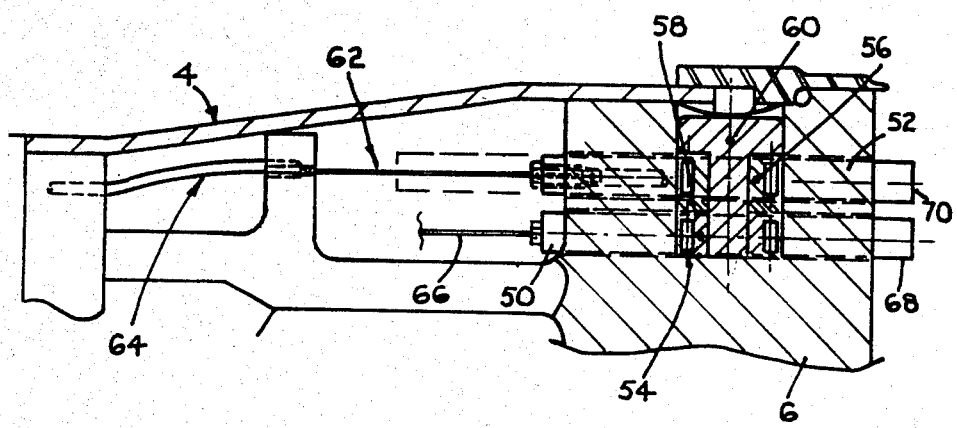
Figure 10:
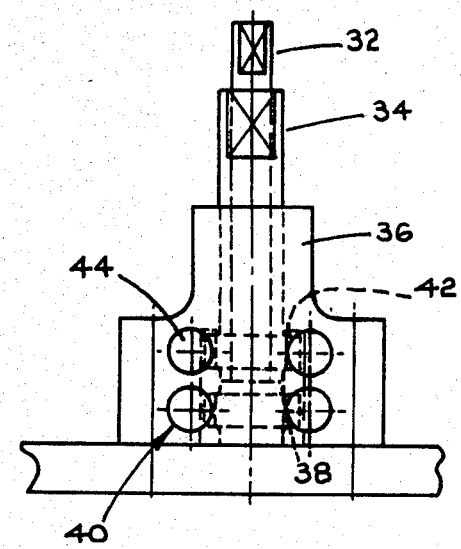
Figure 11:
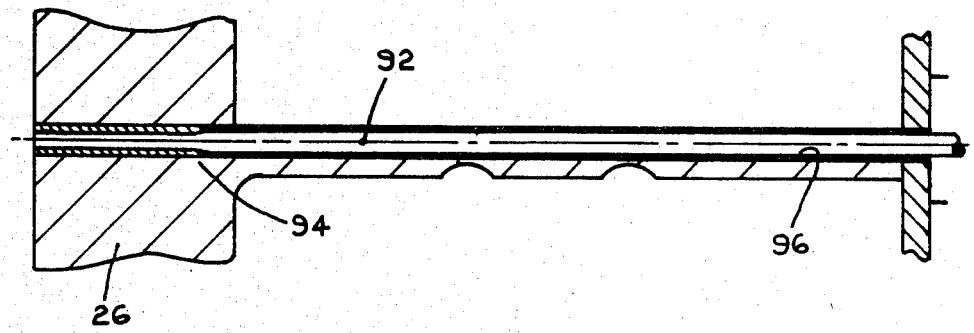
Figure 12:
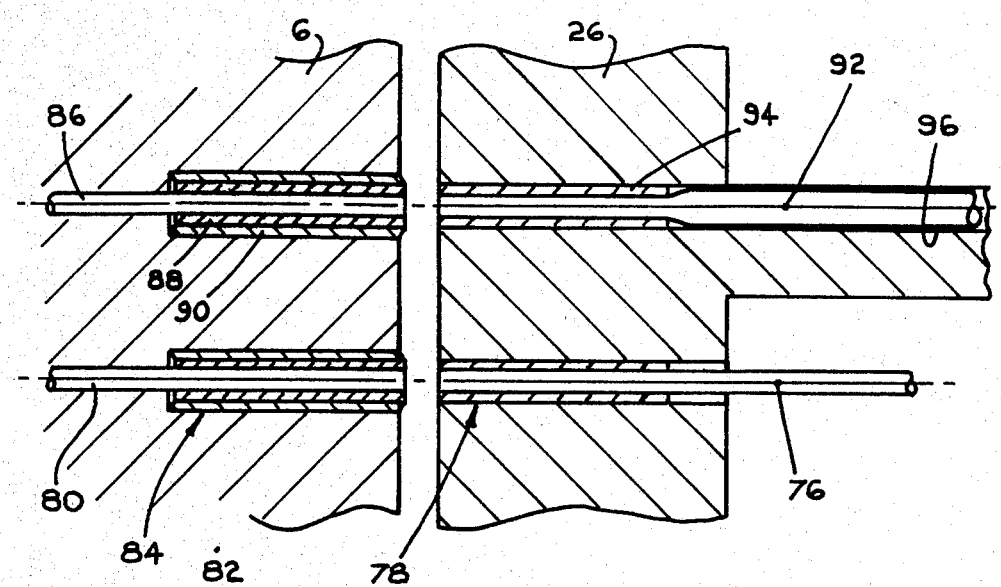
Figure 13:
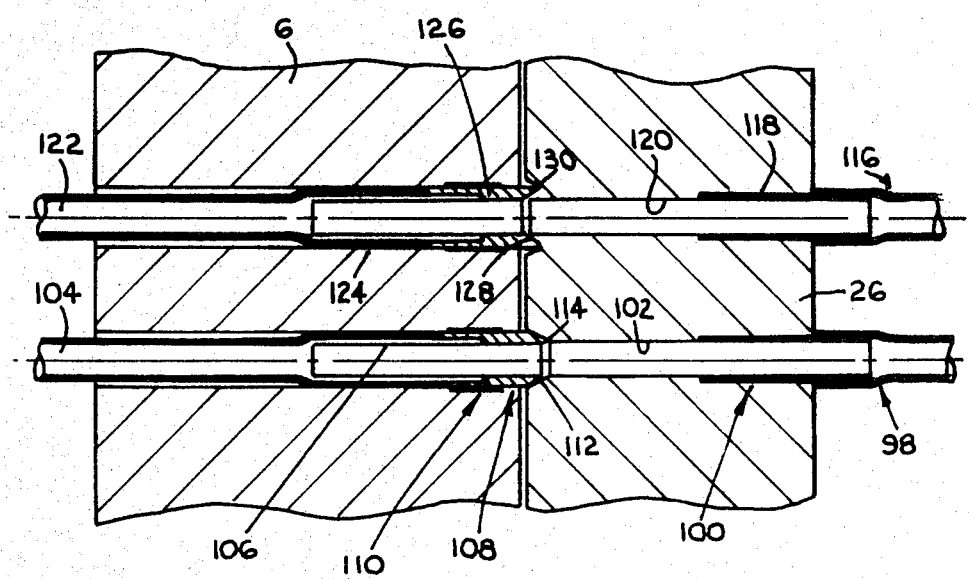
Figure 14:
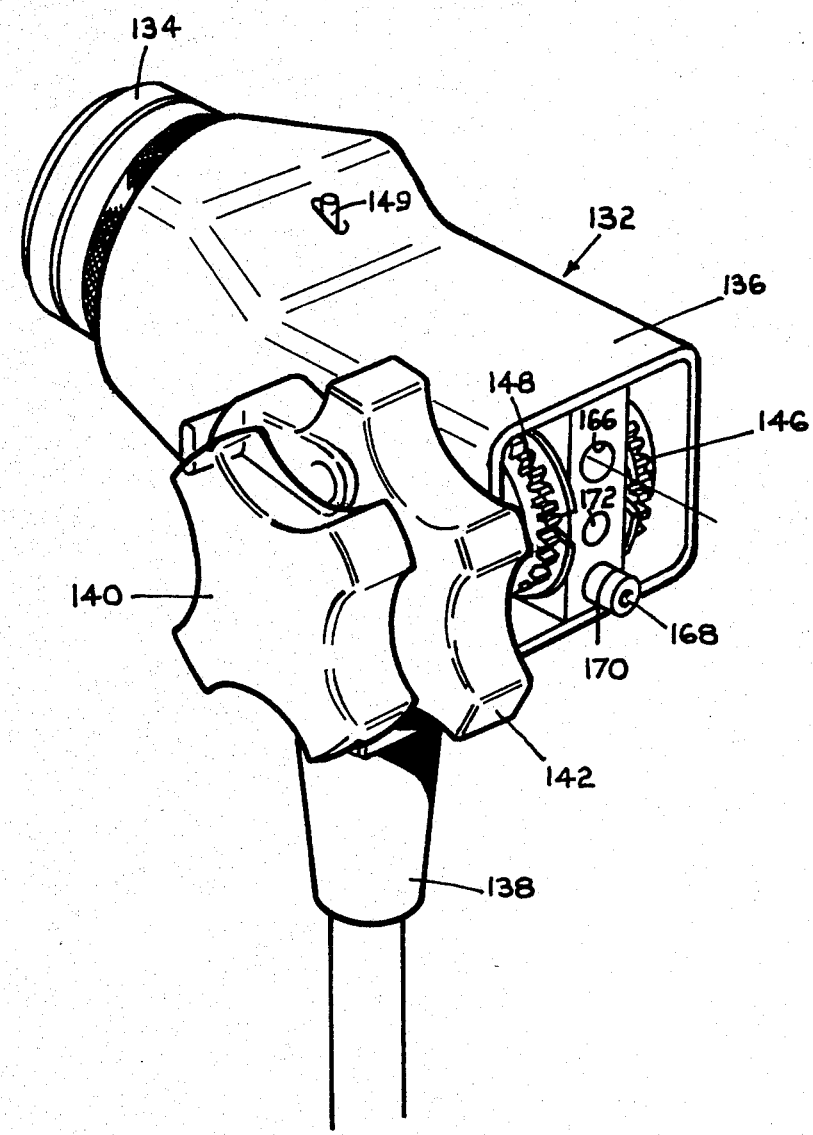
Figure 15:
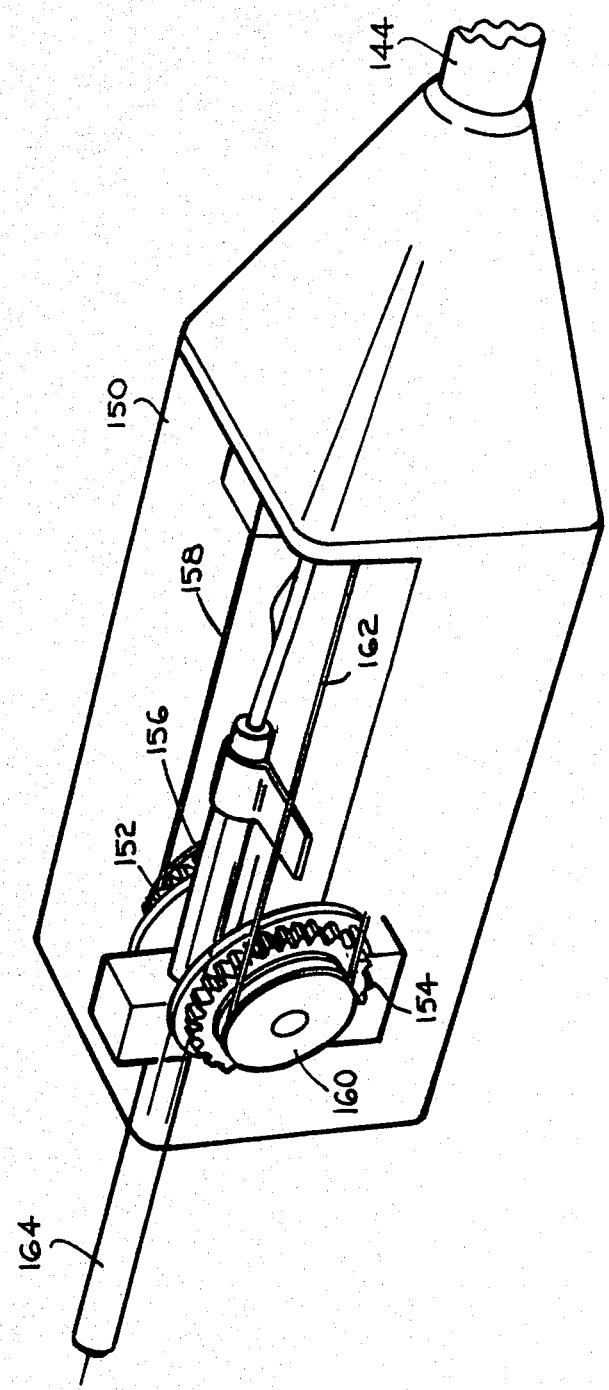
Figure 16A:
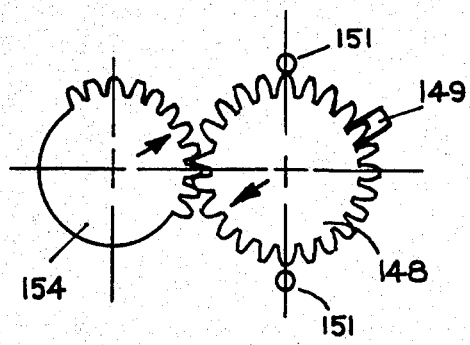
Figure 16B:
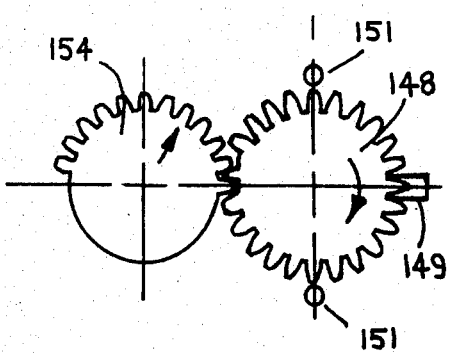
Figure 16C:
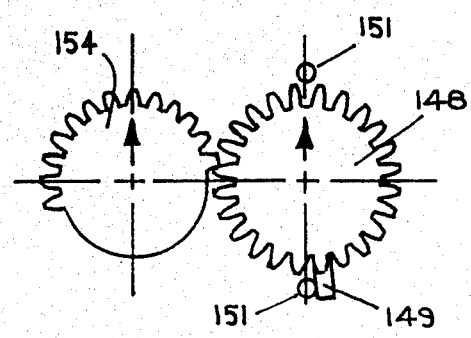
Figure 16D:
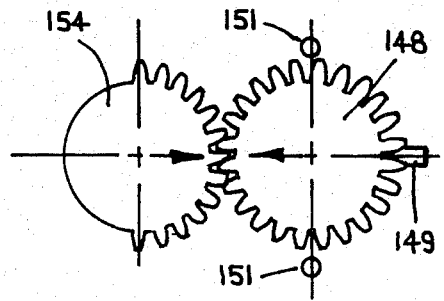
Figure 17:
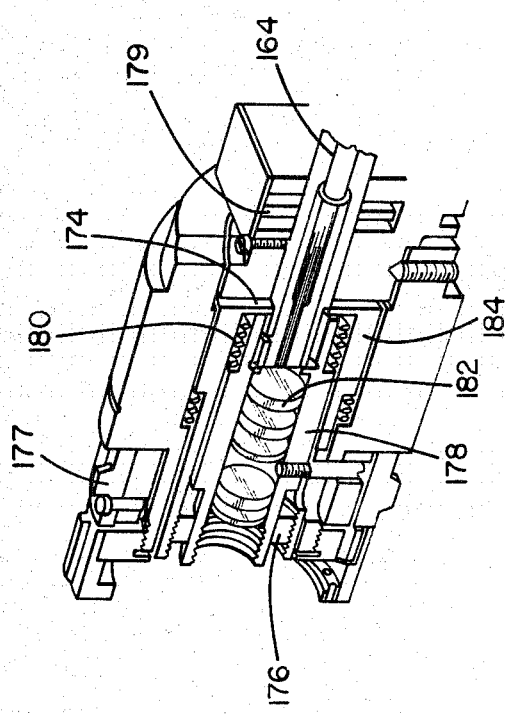

FIG. 7 corresponds to a combination of FIGS. 5 and 6, but with the handle and shaft coupled together;

FIG. 8 is a fragmentary sectional side view showing internal detail of the handle;

FIG. 9 is a fragmentary sectional side view showing internal detail of the shaft;

FIG. 10 is a transverse sectional view taken on the line X—X of FIG. 8;

FIG. 11 is a sectional side view showing a fused fiber optic bundle in the handle;

FIG. 12 is a sectional side view showing how the illumination and image fiber optic bundles are coupled between the shaft and handle;

FIG. 13 is a sectional plan view showing how air/water and biopsy tubes of the endoscope are coupled together;

FIGS. 14 and 15 respectively show the handle and shaft of an alternative embodiment of endoscope according to the invention; and FIGS. 16 and 17 show two modifications.

DETAILED DESCRIPTION OF THE DRAWINGS

Figure 1:
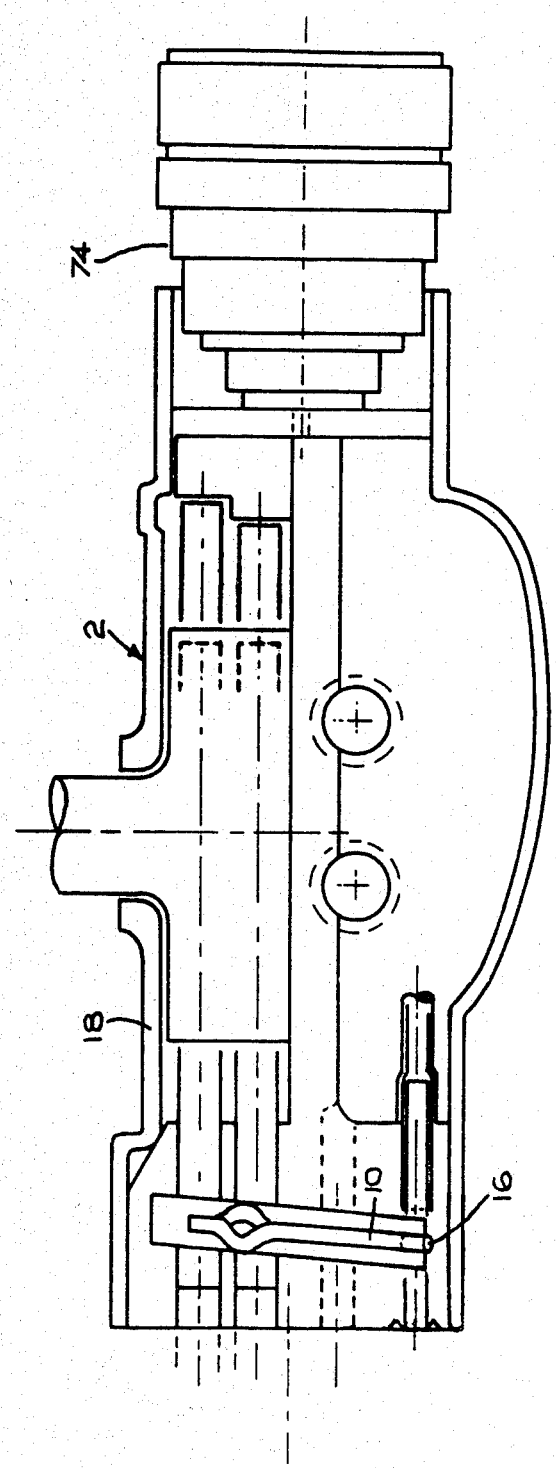
FIG. 1 is a sectional side view of a handle of the endoscope.
Figure 2:
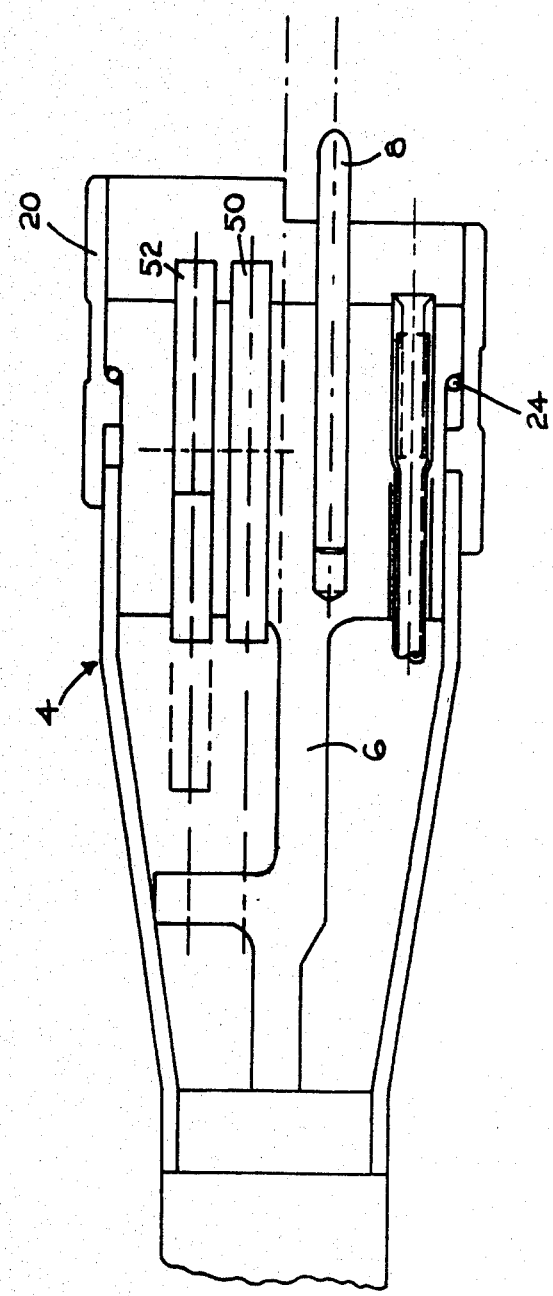
FIG. 2 is a fragmentary side view showing the proximal end of the endoscope shaft which is detachably connected to the handle.

Referring principally to FIGS. 1 and 2, the endoscope has a handle 2 and a shaft 4. The end of the shaft 4, shown in FIG. 2, has a rigid body 6, but the main length of the shaft, extending towards the left in FIG. 2, is flexible and terminates in an operative end having the facilities previously mentioned for viewing a subject within an internal body cavity. To enable the endoscope to work, a number of functions must be transmitted across the coupling faces (shown in FIGS. 3 and 4) between the shaft 4 and handle 2, and the handle and shaft must be capable of being reliably and repeatedly engaged and detached.

FIGS. 5 and 7 show the mechanical coupling means for coupling the shaft and handle. The shaft 4 has two projecting pins, one of which is shown at 8. The handle 2 has two pivotally movable latches for respective cooperation with the pins 8, one of the latches being shown at 10 in FIGS. 1, 4, 6 and 7. Each latch 10 has a circular aperture 12 and is urged by a spring 14 to the locking position shown in FIG. 6. An integrally formed projection or protrusion of the latch 10 constitutes a pin 16 which projects through an external casing 18 of the handle 2. The shaft 4 has a locking device comprising a sleeve 20 formed with two grooves 22 to receive the pins 16. A rubber ring 24 is located between the sleeve 20 and the body 6 of the shaft. When the shaft 4 and handle 2 are coupled together, each pin 8 enters the aperture 12 in the corresponding latch 10 which pivots slightly against the loading of the spring 14 until the pin 8 is fully inserted (FIG. 7). The pin 8 cannot be withdrawn because the latch 10 frictionally engages the pin 8. The sleeve 20 is moved with a bayonet-like action so that the pins 16 enter the grooves 22, thus providing a further lock and preventing any tendency for the pins 8 to be released from the latches 10 as a result of vibration or inadvertent releasing movement of the pins 16. When the sleeve 20 is in the locked position, the ring 24 is compressed between the sleeve 20 and the body 6, as shown in the upper half of FIG. 2 and in FIG. 7, the ring 24 therefore acting as a spring.

Figure 3:
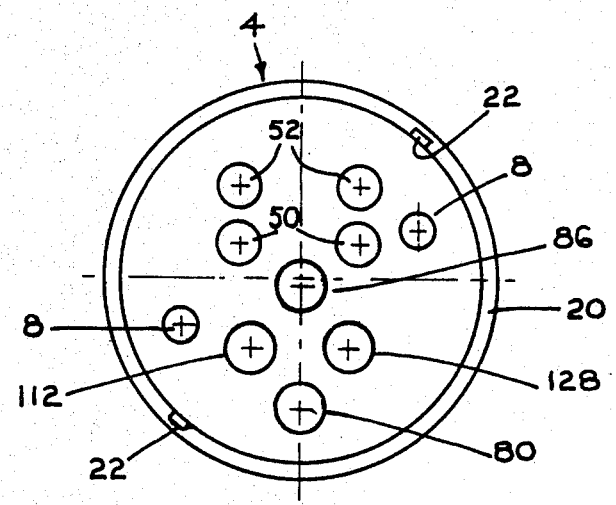
FIG. 3 is an end view of the coupling face of the shaft.
Figure 4:
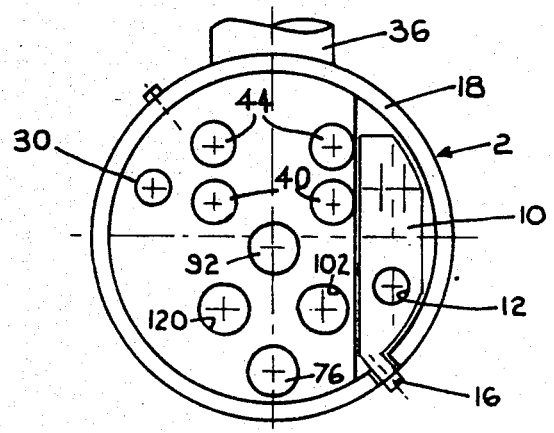
FIG. 4 is an end view of the coupling face of the handle, the right-hand side of the drawing being cut away to reveal a latch.

FIG. 3 shows the coupling face of the shaft 4 and illustrates the two pins 8. FIG. 4 shows the coupling face of the handle 2 and illustrates one latch 10 with its associated aperture 12, such that the apertures 12 are disposed diametrically opposite one another. To accommodate the two latches 10, a body 26 of the handle is formed with recesses 28 shaped as in FIGS. 6 and 7, the body 26 having holes 30 for the passage of the respective pins 8.

Reference will now be made to FIGS. 8 to 10 to explain how controlled flexing of the shaft 4 is achieved by manual adjustment of flexure control means on the handle 2. The flexure control means comprises two manually rotatable wheels (not shown) respectively mounted on concentric spindles 32, 34 (FIG. 8) received within a bearing 36 attached to the body 26 of the handle 2. The inner spindle 32 carries, at its lower end, a pinion 38 meshing with two spaced racks 40. The outer spindle 34 similarly carries a pinion 42 meshing with two spaced racks 44. When the spindle 32 is rotated by the corresponding handwheel, one of the racks 40 moves towards the right (as viewed in FIG. 8) and the other towards the left. Similarly, when the spindle 34 is rotated, one of the racks 44 moves towards the right and the other towards the left. The spindles 32, 34 are independently rotatable so that the pairs of racks 40, 44 can be moved independently. In a neutral or datum position of the wheels attached to the spindles 32, 34 (corresponding to a substantially straight condition of the shaft 4), the ends 46, 48 of the racks 40, 44 are recessed within the body 26 of the handle 2, as indicated in FIG. 8.

The sliding motions of the pairs of racks 40, 44 are transmitted to two further pairs of racks 50, 52 (FIG. 9), slidably mounted on the body 6 of the shaft 4. The first pair of racks 40 are interconnected by a pinion 54, and the second pair of racks 52 are interconnected by a further pinion 56. Hence, as one rack 50 moves towards the left, the other rack 50 moves towards the right, and vice versa. The two racks 52 of the other pair similarly move in mutually opposite directions by virtue of the pinion interconnecting them. The pinions 54, 56 are mounted for independent rotation on an idler bearing 60 and are separated by a bearing washer 58. The two racks 52 are attached to the ends of two tension elements in the form of wires 62 which extend through sleeves 64 into the shaft 4. Similarly, the two racks 50 are attached to the respective ends of two wires 66.

When the shaft and handle are coupled together, the ends 46 of the racks 40 abut the ends 68 of the racks 50, and the ends 48 of the racks 44 abut the ends 70 of the racks 52. Adjusting movement of the spindle 32 is then transmitted from the handle 2 to the shaft 4 as a result of one of the racks 40 pushing the abutting one of the racks 50 towards the left, as viewed in FIG. 9, the other rack 40 moving to the right to accommodate rightwards movement of the other rack 50. Similarly, adjusting movement of the spindle 34 is transmitted across the handle/shaft interface as a result of one of the racks 44 pushing the abutting rack 52.

In each case, pushing movement of one of the racks 40 and one of the racks 44 is converted, by the rack and pinion mechanisms on the shaft, into a pulling action on one of the wires 62. The two wires 62 control flexing of the shaft in one plane, whilst the two wires 66 control flexing of the shaft in the orthogonal plane. In consequence, controlled rotation of the two wheels on the spindles 32, 34 enables the operative end of the endoscope to be adjusted independently in the two mutually orthogonal planes.

It will be appreciated from FIG. 2 that the ends of the racks 50, 52 which project from the shaft in the neutral position of flexure are protected by the sleeve 20. An end stop 72 in the handle 2 defines the limits of movement of the racks 40, 44 and therefore the amplitude of movement of the racks 50, 52.

As previously explained, light is transmitted from a source, through the handle, and down the shaft to the operative end of the endoscope, to illuminate the subject being viewed. Light reflected from the subject is transmitted back along the shaft and through the handle to an eyepiece generally indicated at 74 in FIG. 1. Instead of an eyepiece, the endoscope handle may have a camera for recording the image, or any means for transmitting the image to another location. In all cases, the handle has an image-receiving plane at which the image is received.

FIGS. 11 and 12 illustrate how the illumination light is coupled from the handle to the shaft, and how the image is coupled from the shaft to the handle. Illumination light passes through a fiber optic bundle 76 (FIG. 12) extending within a stainless steel ferrule 78 located in a bore in the body 26 of the handle 2. At the coupling face, the end of the bundle 76 is aligned with the end of a further fiber optic bundle 80 surrounded by a stainless steel ferrule 82 sheated by a rubber sleeve 84. The bundle 76 may be larger (e.g. ten percent) in cross-sectional area than the bundle 80 to ensure full illumination of the fiber optic bundle end in the shaft if slight misalignment is present. The fiber optic bundle 80 extends within a bore in the shaft body 6, this bore being counterbored to receive the ferrule 82 and the sleeve 84. The fiber optic bundle 80 is flexible and extends along the shaft to the operative end of the endoscope.

The image is transmitted along the shaft 4 from the operative end by a further flexible fiber optic bundle 86 which, adjacent the coupling face of the shaft, is surrounded by a stainless steel ferrule 88 and a rubber sleeve 90. The end of the fiber optic bundle 86 is aligned with the end of a fused fiber optic bundle 92 which first passes through a stainless steel ferrule 94 within a bore in the body 26 and then emerges to extend along a straight groove 96 leading the fiber optic bundle 92 to the eyepiece 74. Setting the fused fiber bundle 92 within the groove 96 protects the bundle 92 from damage during assembly or servicing.

When the handle and shaft are coupled together, the ends of the fiber optic bundles 76 and 80 abut so that light is transmitted across the interface with little loss. Similarly, the image-carrying fiber optic bundles 86 and 92 abut, this being a more critical interface than for the bundles 76 and 80 because of the need to transmit a coherent image with the minimum loss or distortion. Effective optical coupling between the bundles 76, 80 and 86, 92 is achieved by making the ends of the bundles 80 and 86 project a small distance from the coupling face of the shaft, and by the provision of the rubber sheaths 84, 90 which, on coupling, are compressed and act in the manner of springs to urge the ends of the bundles 76, 80 into close abutting relationship and, more importantly, the ends of the bundles 86, 92 into close abutting relationship.

Two further passages are also provided through the handle and shaft, one for air and water and the other for biopsy. The coupling of these passages across the handle/shaft interface is illustrated in FIG. 13. A plastic tube 98 for air or water is fitted over a stainless steel ferrule 100 communicating with a bore 102 in the handle body 26. An aligned plastic tube 104 in the shaft is fitted over a stainless steel tube 106 bonded to a resilient elastomeric sleeve 108 bonded to the shaft body 6 at 110. The sleeve 108 has a tapering end 112 projecting from the coupling face of the shaft 4. The coupling face of the handle 2 has a cooperating tapering recess 114 acting as a counterbore for the bore 102.

A further plastic tube 116, similar to the tube 98, is for biopsy purposes. The tube 116 is fitted over a stainless steel ferrule 118 communicating with a bore 120 in the handle body 26. The aligned tube 122 in the shaft body 6 is fitted over a stainless steel tube 124, an end portion of which is surrounded by a resilient elastomeric sleeve 126 bonded to the body 6. The end 128 of the sleeve 125 is tapered, or chamfered, in the opposite direction to the end 112, and the coupling face of the handle has a circular groove 130 (concentric with the bore 120) to receive the projecting end 128 of the sleeve 126.

Sealing at the coupling faces is achieved by compression of the ends 112, 128 against the cooperating shapes of the recess 114 and groove 130, this being adequate for the low pressures involved.

FIGS. 14 and 15 show an alternative embodiment which may be preferred to the embodiment of previous figures. The handle 132 (FIG. 14) has an eyepiece 134 at one end of casing 136 which is of square or rectangular cross-sectional shape. An "umbilical" lead 138 conducts the necessary services to the handle 132. Two manually rotatable wheels 140, 142 provide for controlled flexing of the flexible shaft 144 (FIG. 15) in two mutually orthogonal planes. The two wheels 140, 142 are coaxial and respectively drive two pinions 146, 148. The handle 132 has a single latch (not shown), the projecting pin 149 of which can be seen in FIG. 14. The pin 149 corresponds to one of the pins 16 in the previous embodiment.

Referring to FIG. 15, the proximal end of the flexible length of the shaft 144 is attached to a casing 150 having two rotatably mounted pinions 152, 154. The pinion 152 has attached thereto a drum 156 around which passes a wire 158, the two runs of which provide the two tension elements for flexing the shaft 144 in one of the two mutually orthogonal planes. Similarly, the pinion 154 has attached thereto a drum 160 around which passes a wire 162, the two runs of which provide the two tension elements for flexing the shaft 144 in the other of the two mutually orthogonal planes.

When the handle and shaft are brought together, the pinion 146 meshes with the pinion 152, and the pinion 148 meshes with the pinion 154. Hence, rotation of the wheel 140 is transmitted by the meshing pinions 146 and 152 to the drum 156 which rotates to move the tension elements 158 so as to flex the shaft 144. Rotation of the other wheel 142 moves the tension elements 162 to flex the shaft 144 in the alternative plane.

The image is transferred from the shaft to the handle by a fiber optic bundle received within a rigid sleeve 164 projecting from the proximal end of the shaft. The sleeve 164 is inserted in a bore 166 in the handle, the end of the fiber optic bundle transmitting the image to the eyepiece 134. The sleeve 164 performs the function of one of the pins 8 of the previous embodiment in that the sleeve 164 engages within an aperture in the latch to provide mechanical coupling of the handle and shaft. Release is effected by movement of the release pin 149 which tilts the latch against its spring loading, as in the previous embodiment. Hence, in FIGS. 14 and 15 the rigid sleeve 164 (with its fiber optic bundle therein) is withdrawn from the handle when the shaft and handle are separated.

A tubular spigot 168, on the handle, locates in a recess (not shown) in the shaft to provide interconnection of air, water, or suction. The spigot 168 has an 0-ring seal 170 and, with the sleeve 164, ensures that the handle and sleeve are coupled together in the correct orientation.

Illuminating light is conducted from the handle to the shaft by abutting fiber optic bundles, as in the previously described embodiment, the fiber optic bundle on the handle being shown at 172 in FIG. 14.

When the handle 132 and shaft 144 are assembled, it is desirable that there should be a predetermined relationship between the articulation of the endoscope shaft and the position of the control wheels 140, 142. This is achieved by means which relate the rotational position of the wheels or pinions on the shaft and handle. All the operator has to do, after assembly, is to turn each control wheel 140, 142 through its complete travel. This is shown in FIG. 16 which shows the two drive pinions 148, 154, the latter having been modified compared with FIG. 15 by having half its periphery devoid of teeth. The other pair of pinions 146, 152 are brought to a predetermined position in the same manner. In FIG. 16(a) the two gear wheels or pinions 148, 154 have been brought together in a random fashion. In FIG. 16(b) the control wheel 148 has been turned part way through its travel and the interrupted gear 154 in the shaft has reached the end of its travel (corresponding to maximum articulation). Further rotation of the control wheel 148 to the end of its travel, FIG. 16(c), occurs without additional movement of the interrupted gear 154, as it has reached the blank part of the gear. The limits of rotation of the wheel 148 are defined by the abutment of a radial projection 149 with one of two stops 151. When the control wheel 148 is released, the natural springiness of the endoscope shaft causes the interrupted gear 154 to mesh with the control wheel gear 148, and the two wheels, 148, 154, are now correctly aligned.

This alignment is maintained and cannot be altered without removing the shaft from the handle.

When the endoscope is used with a camera attached to the eyepiece via an adaptor, it is necessary to control the distance between the eyepiece lens and the end of the image bundle very accurately in order to focus the image.

In conventional, non-modular instruments this is done by careful adjustment during assembly. In the modular instrument of the present invention, where the image bundle forms part of the shaft and the eyepiece part of the handle, the instrument design needs to achieve this accurate relationship each time any shaft is coupled to any handle.

This is done in the following way, referring to FIG. 17. In the shaft, the sleeve 164, surrounding the image bundle, has a shoulder 174. In the handle, a screwed collar 176, at the rear of the eyepiece assembly, is adjusted so that, when a lens barrel 178 is pushed right back by a spring 180, the distance between the eyepiece lens 182 and the front of a barrel sleeve 184 is also fixed to a set value.

When the shaft and handle are fitted together, the last part of the movement causes the shoulder 174 on the image bundle pin to come into contact with the barrel sleeve 184 and push it backwards against the spring 180, thus holding the image bundle end to eyepiece lens distance to its preset value.

FIG. 17 shows a focus ring 177 and the tilting latch 179 corresponding to the latch 10 shown on earlier figures.

It will be appreciated that the various coupling means, shown in the embodiments, may be combined in different ways. For example, it is possible for the image coupling and mechanical coupling of FIGS. 14 and 15 to be used in association with the racks of FIGS. 8 and 9.

The coupling of the various functions ensures that the handle and shaft are coupled together in the correct angular orientation in both of the embodiments described. However, it is possible for this correct angular orientation to be assured by the design of the mechanical coupling means alone, or the design of the passages providing for air, water, or biopsy, or by a combination of these.

We claim:

1. An endoscope having a handle, a shaft with a flexible length terminating in a distal end, a proximal end of the shaft having a coupling face for detachable connection to a coupling face of the handle and the distal end of the shaft being arranged to receive an optical image of a subject to be viewed, flexure control means operable on the handle for effecting controlled flexing of the shaft, first coupling means for mechanically coupling the shaft and handle, the first coupling means being capable of being released to allow the shaft and handle to be separated, second coupling means for transmitting illuminating light from the handle to the shaft, third coupling means for transmitting an optical image from the shaft to the handle, and fourth coupling means for transmitting from the handle to the shaft movement providing for the controlled flexing of the shaft.

2. An endoscope according to claim 1 wherein the first coupling means allows the shaft and handle to be pushed together but automatically prevents relative withdrawing movement of the shaft and handle.

3. An endoscope according to claim 1 wherein the first coupling means comprises a pivotally movable spring-loaded latch having an aperture, and a cooperable latch pin which passes through the aperture when the shaft and handle are pushed together, the latch frictionally engaging the latch pin to prevent separation of the shaft and handle.

4. An endoscope according to claim 3 wherein the latch is mounted in the handle and the pin in the shaft.

5. An endoscope according to claim 3 wherein the latch is movable to a release position, against the spring-loading on the latch, by manual movement of a release member operatively connected to or forming part of the latch.

6. An endoscope according to claim 5 wherein the release member is an extension of the latch.

7. An endoscope according to claim 3 wherein the latch and pin ensure the correct angular orientation of the handle and shaft as the latter are coupled together or contribute towards the correct angular orientation being achieved.

8. An endoscope according to claim 3 wherein the latch pin is one of a plurality of such pins and the latch is one of a plurality of such latches.

9. An endoscope according to claim 5 wherein a locking device is provided to retain the release member so as to prevent the latter being moved inadvertently to the release position.

10. An endoscope according to claim 1 wherein the third coupling means comprises a fiber optic bundle in the handle and a flexible fiber optic bundle in the shaft, at the coupling faces, the fiber optic bundles presenting ends which make face to face contact, or are brought into close face to face relationship, when the shaft and handle are connected together.

11. An endoscope according to claim 3 wherein the third coupling means comprises a fiber optic bundle in the handle and a flexible fiber optic bundle in the shaft, at the coupling faces, the fiber optic bundles presenting ends which make face to face contact, or are brought into close face to face relationship, when the shaft and handle are connected together.

12. An endoscope according to claim 11 wherein the fiber optic bundle in the handle is a fused fiber optic bundle which extends from the coupling face of the handle to an image-receiving plane in the handle, the handle being formed with a groove to receive the fused fiber optic bundle.

13. An endoscope according to claim 11 wherein the flexible fiber optic bundle in the shaft is surrounded by a sleeve of resilient material at the coupling face of the shaft, the resilient sleeve acting as a spring and facilitating face to face contact between the ends of the fiber optic bundles.

14. An endoscope according to claim 1 wherein the third coupling means comprises a fiber optic bundle which extends from the shaft to an image-receiving plane in the handle, the length of fiber optic bundle within the handle being withdrawn therefrom when the shaft is separated from the handle.

15. An endoscope according to claim 3 wherein the third coupling means comprises a fiber optic bundle which extends from the shaft to an image-receiving plane in the handle, the length of fiber optic bundle within the handle being withdrawn therefrom when the shaft is separated from the handle.

16. An endoscope according to claim 15 wherein said length of fiber optic bundle is surrounded by a rigid sleeve which constitutes said pin.

17. An endoscope according to claim 15 wherein means are provided to set accurately the distance between the end of the fiber optic bundle within the handle and an eyepiece lens of the handle each time the handle and shaft are coupled together.

18. An endoscope according to claim 3 wherein the third coupling means comprises a flexible fiber optic bundle in the shaft and a lens within the handle, the lens transmitting the image from the coupling face of the handle to an image-receiving plane in the handle.

19. An endoscope according to claim 3 wherein the fourth coupling means relies on a pushing movement being transmitted from the handle to the shaft, reversing means being provided in the shaft to convert the pushing movement into a pulling movement applied to tension elements which extend within the shaft and which are operative when pulled to flex the shaft.

20. An endoscope according to claim 19 wherein the reversing means comprises a pair of racks interconnected by a pinion, a pushing action on one of said racks being converted into a pulling action on the other of said racks by means of the pinion.

21. An endoscope according to claim 20 wherein the pushing action is applied to said one rack in the shaft by one of a further pair of racks mounted in the handle, the further pair of racks mounted in the handle being interconnected by a pinion which is coupled to said flexure control means.

22. An endoscope according to claim 21 wherein the pair of racks and pinion in the shaft constitute one rack and pinion assembly of two such assemblies for flexing the shaft in two mutually orthogonal planes, respectively, the pair of racks and associated pinion in the handle similarly forming one rack and pinion assembly of two such assemblies independently adjustable by the flexure control means.

23. An endoscope according to claim 1 wherein the fourth coupling means comprises members rotationally mounted on the shaft and handle, the members interengaging to transmit rotational movement from the member on the handle to the member on the shaft when the shaft and handle are coupled together.

24. An endoscope according to claim 3 wherein the fourth coupling means comprises members rotationally mounted on the shaft and handle, the members interengaging to transmit rotational movement from the member on the handle to the member on the shaft when the shaft and handle are coupled together.

25. An endoscope according to claim 15 wherein the fourth coupling means comprises members rotationally mounted on the shaft and handle, the members interengaging to transmit rotational movement from the member on the handle to the member on the shaft when the shaft and handle are coupled together.

26. An endoscope according to claim 25 wherein the members of the fourth coupling means are toothed wheels mounted respectively on the coupling faces of the handle and of the shaft, the toothed wheels making meshing engagement when the shaft and handle are coupled together.

27. An endoscope according to claim 26 wherein means are provided to relate the rotational positions of the toothed wheels after assembly of the shaft and handle.

28. An endoscope according to claim 25 wherein passages for air, water, and biopsy extend through the handle and shaft, these passages being coupled across the coupling faces of the handle and shaft.

29. An endoscope according to claim 28 wherein the coupling of said passages ensures the correct orientation of the handle and shaft, or contributes towards this correct angular orientation being achieved.

* * * * *